United States Patent
Solli et al.

(10) Patent No.: US 8,174,690 B2
(45) Date of Patent: May 8, 2012

(54) APPARATUS FOR CHARACTERIZING A SURFACE STRUCTURE

(75) Inventors: Vidar Solli, Kongsberg (NO); Kaj-Robin Weslien, Kongsberg (NO)

(73) Assignee: Argos Solutions AS, Kongsberg (NO)

( * ) Notice: Subject to any disclaimer, the term of this patent is extended or adjusted under 35 U.S.C. 154(b) by 48 days.

(21) Appl. No.: 12/599,271

(22) PCT Filed: May 8, 2008

(86) PCT No.: PCT/NO2008/000161
§ 371 (c)(1),
(2), (4) Date: Feb. 5, 2010

(87) PCT Pub. No.: WO2008/140321
PCT Pub. Date: Nov. 20, 2008

(65) Prior Publication Data
US 2010/0201973 A1    Aug. 12, 2010

(30) Foreign Application Priority Data
May 11, 2007   (NO) .................................... 20072448

(51) Int. Cl.
*G01N 21/00* (2006.01)
(52) U.S. Cl. ................... 356/237.2; 356/237.3
(58) Field of Classification Search ..... 356/237.1–237.6
See application file for complete search history.

(56) References Cited

U.S. PATENT DOCUMENTS

| | | | |
|---|---|---|---|
| 3,877,814 A | 4/1975 | Hess et al. | |
| 5,016,099 A | 5/1991 | Bongardt et al. | |
| 5,432,331 A | 7/1995 | Wertheimer | |
| 5,644,392 A | 7/1997 | Soest et al. | |
| 5,914,490 A | 6/1999 | Sumen et al. | |
| 2001/0001573 A1 | 5/2001 | Haga et al. | |
| 2005/0052644 A1* | 3/2005 | Lewis et al. | 356/237.4 |
| 2007/0103688 A1 | 5/2007 | Kuusela | |

FOREIGN PATENT DOCUMENTS

| | | |
|---|---|---|
| JP | 7-91931 | 4/1995 |
| WO | WO 98/36264 | 8/1998 |
| WO | WO 00/39566 | 7/2000 |
| WO | WO 0006838 A1 | 11/2000 |
| WO | WO 0120308 A1 | 3/2001 |
| WO | WO 2004/034041 | 4/2004 |
| WO | WO 2005/116579 | 12/2005 |

* cited by examiner

*Primary Examiner* — Tri T Ton
(74) *Attorney, Agent, or Firm* — Knobbe, Martens, Olson & Bear, LLP

(57) ABSTRACT

An apparatus for optically characterizing a surface structure of a board or sheet, includes a light source arranged at a first side of a said board and adapted to illuminate a first area of a surface of said board or sheet by emitting towards said surface a collimated light beam at a first, oblique angle of incidence relative to said surface of said board or sheet. A light receiver arranged at a second side of a said board or sheet, said second side being substantially opposite to said first side in respect of said board or sheet, is adapted to receive at least a part of said collimated light beam being reflected off said first area of said surface of said board or sheet, and includes a spatial detector adapted to receive by different parts of said detector light of said collimated light beam being reflected off respective, different parts of said first area.

5 Claims, 5 Drawing Sheets

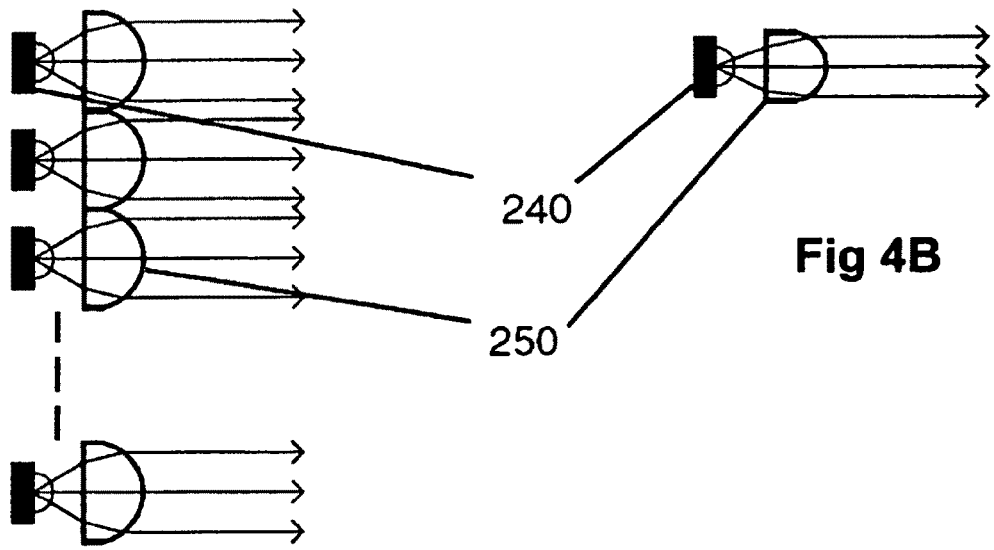
240
250
Fig 4B
Fig 4A
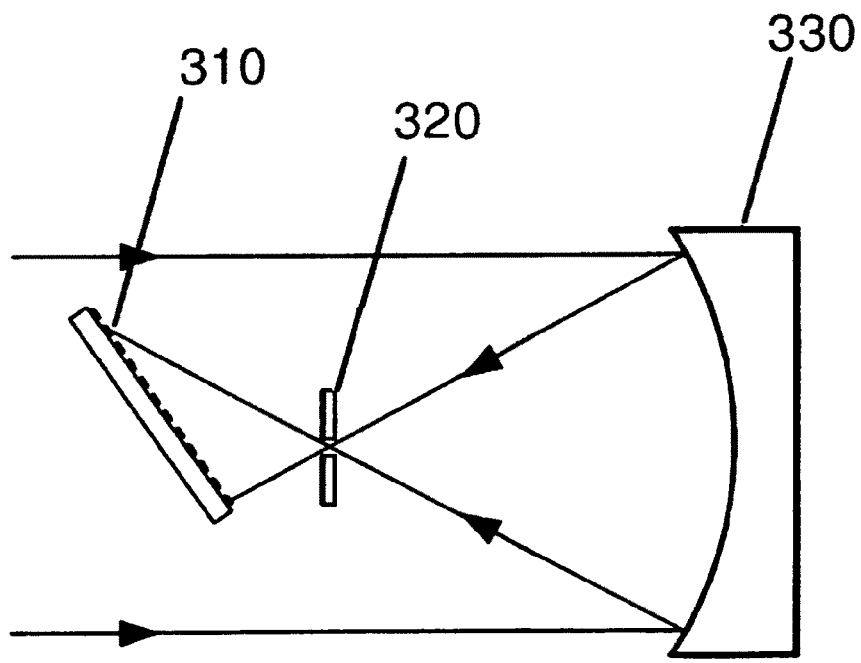
Fig 5

Section A – A
(ref. fig. 6A)

APPARATUS FOR CHARACTERIZING A SURFACE STRUCTURE

CROSS-REFERENCE TO RELATED APPLICATIONS

This application claims the benefit and priority to and is a U.S. National Phase of PCT International Application Number PCT/NO2008/000161, filed on May 8, 2008. This application claims the benefit and priority to Norwegian Application No. NO 20072448, filed on May 11, 2007. The disclosures of the above-referenced applications are hereby expressly incorporated by reference in their entirety.

BACKGROUND OF THE INVENTION (1) Field of the Invention

The apparatus of the invention relates to the field of optically characterizing the structure of a surface, which, for example, is useful in a board or sheet production line for inspecting the quality of a board or sheet product.

A known apparatus is disclosed in U.S. Pat. No. 3,694,658 to Morvue, presenting diffuse light transversal to the element under inspection and its direction of which t is conveyed, wherein light reflected off a surface of the element under inspection is picked up by a plurality of optical fibers. A conveyor conveys the board or sheet past an elongated light source, such as a fluorescent light tube, located in a first position over the board or sheet, while a light detector is located over the board or sheet in a second position spaced from the first position in a direction of conveyance of the board or sheet. An elongated aperture or baffle is arranged between the light source and the detector, such that the detector may only receive such light from the light source that has been reflected off or scattered by the surface of the board or sheet and that has a significant directional component corresponding to the direction of conveyance of the board or sheet.

(2) Description of Related Art

Other known art is disclosed in U.S. Pat. No. 5,252,836 to US National resources, illustrating surface inspection using collimated light propagating in the direction in which an element under inspection is conveyed.

BRIEF SUMMARY OF THE INVENTION

The present invention provides a collimated light source arrangement, an imaging light detector arrangement and a surface inspection device, adapted for inspection of a surface of an element to be inspected, the features of which source arrangement, detector arrangement and inspection device are recited in the accompanying patent claims.

BRIEF DESCRIPTION OF THE SEVERAL VIEWS OF THE DRAWINGS

In the following, the invention will explained by way of example, and with reference to the accompanying drawings, wherein FIG. 4A is a side view drawing of second embodiment of a collimated light source relating to an apparatus of the invention, FIG. 4B is a top view drawing of the collimated light source of FIG. 4A, and FIG. 5 is a side view drawing of an imaging light detector arrangement relating to an apparatus of the invention, and FIGS. 6A and B are perspective and sectional views, respectively, of an embodiment of a collimated light source embodying features of the present invention.

The apparatus of the invention includes a light source 200 arranged at a first side of, for example, a board or sheet 100, and adapted to illuminate a first area 400 of a surface of said board or sheet 100 by emitting towards said surface a collimated light beam at a first, oblique angle of incidence relative to said surface of said board or sheet.

Figure 1:
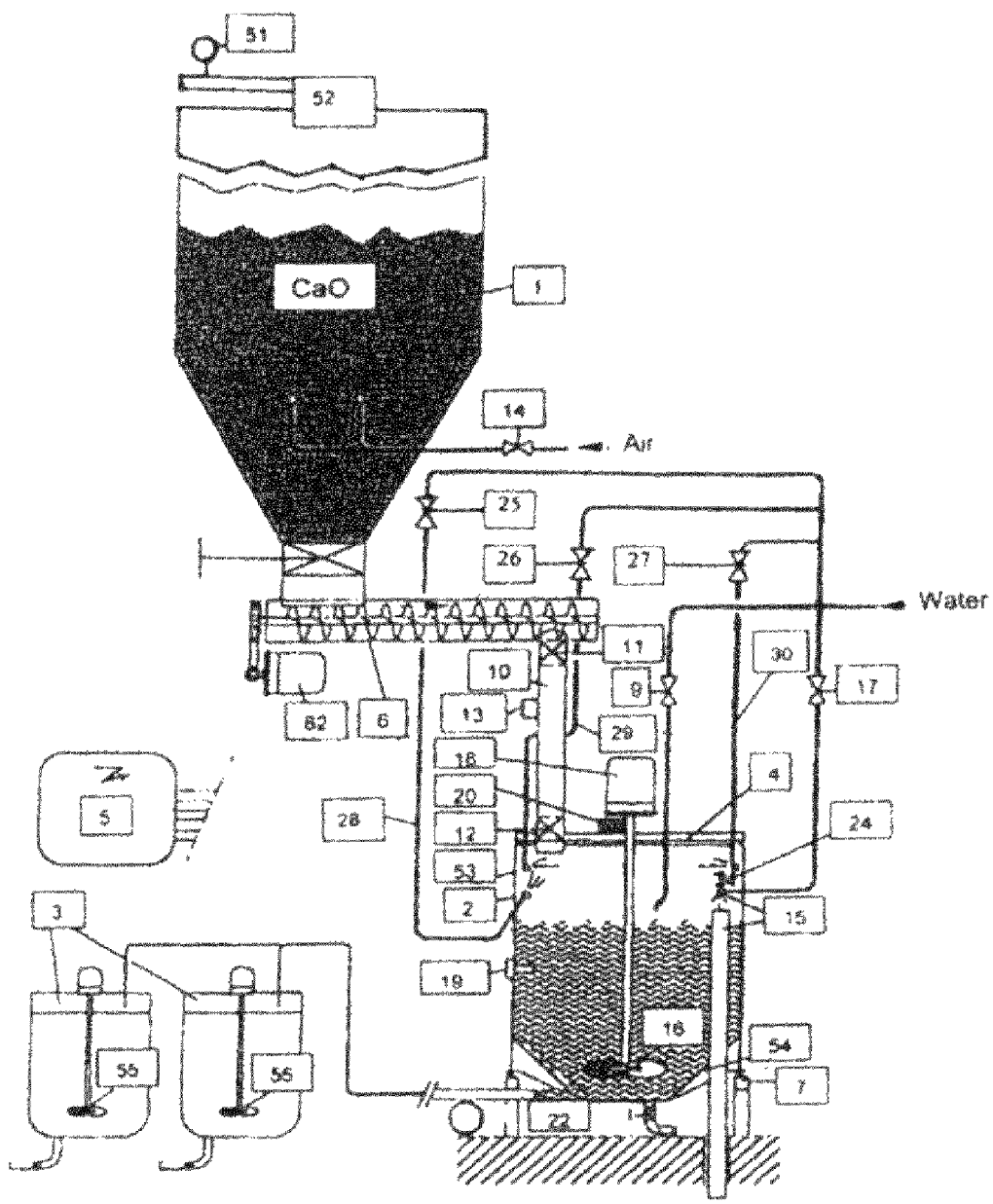
FIG. 1 is a perspective view drawing of a surface inspection device according to the present invention.
Figure 2:
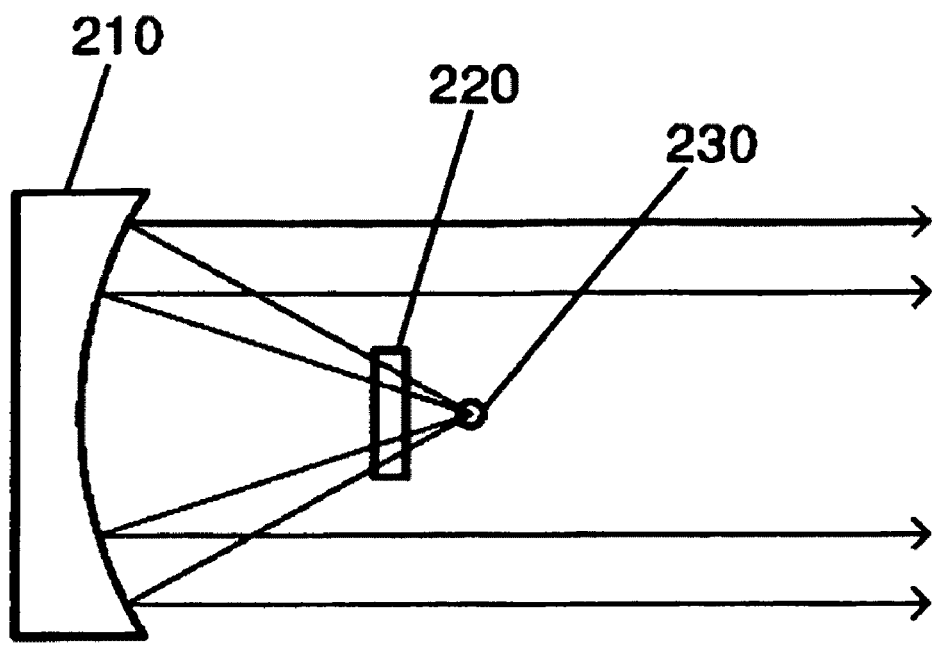
FIG. 2 is a side view drawing of first embodiment of a collimated light source relating to an apparatus of the invention.

In an embodiment of the apparatus disclosed above, the light source includes an optical collimator adapted to provide said light beam as a broad, collimated light beam having an elongated cross section of a first length, and propagating in a first plane indicated by the virtual plane feature 500. It should be noted that the plane 500 shown in FIG. 1 is not a physical feature of the invention, and has been included in FIG. 1 only for the purpose of clarifying the meaning of the term first plane in the context of this disclosure. The elongated cross section of the broad, collimated light beam may be of a substantially rectangular shape, wherein the first length corresponds to the longer side of the rectangle. The width of the beam rectangle is preferably set such that an optimal use of the light energy is obtained by a detector 300 arranged to receive light reflected by the area 400 of the board illuminated by the collimated light beam. Thus, the width of the substantially rectangular beam would correspond to the dimension of the illuminated are 400 extending in the direction of the large arrow shown in FIG. 1. The height of the rectangular beam in the embodiment illustrated in FIG. 1 would be the dimension of the illuminated area 400 across the board or sheet multiplied by tan(5 degrees) for the rectangular beam to illuminate the full width of the board or sheet with the collimated light beam at a 5 degree angle relative to the surface of the board or sheet 100.

The first plane 500 may advantageously be selected to be substantially perpendicular to a plane of said first part of said surface of said board or sheet 100 to be inspected.

In an embodiment of the invention, the first, oblique angle (e.g. as shown by "~5 degree" in FIG. 1) is selected such that the first length when projected onto the first surface becomes substantially equal to or greater than a width of said board or sheet. Thus, the entire surface of the board or sheet may be inspected by way of a single source of collimated light.

The apparatus of the invention may further include a light receiver arranged at a second side of a said board or sheet, said second side being substantially opposite to said first side in respect of said board or sheet, said light receiver adapted to receive at least a part of said collimated light beam being reflected off said first area of said surface of said board or sheet, and including a spatial detector adapted to receive by different parts of said detector light of said collimated light beam being reflected off respective, different parts of said first area.

Advantageously, the light receiver 300 includes an image forming optical means 330 for imaging onto said detector 310 an image of at least a section of said first area, preferably the entire first area when spanning across the sheet or board, said image forming optical means having an optical axis. Generally, the optical axis referred to herein is the optical axis as known by a person skilled in the art of optics concerning lenses and curved reflectors with being regularly shaped, such as typical spherical lenses and mirrors, and other corresponding optical elements adapted to form an optical image of an object.

An apparatus according to the invention may be so designed that the image forming optical means comprises a focusing optical element 330 having its optical axis inclined relative to the first area of the surface at an angle (e.g. .about.5 degrees, as indicated in FIG. 1) that substantially corresponds to an angle (e.g. .about.5 degrees, as indicated in FIG. 1) at which the collimated light beam is reflected off the first area of the surface by specular reflection.

FIGS. 4A and 4B illustrate a further arrangement for a collimated light source suitable for embodying the present invention. The further arrangement, in FIG. 4A in a side view, and in FIG. 4B in a top view, includes an array of light sources 240, each advantageously exhibiting a small area of emission of light, such as e.g. LED or semiconductor lasers, and a corresponding array of optical elements 250, such as e.g. lenses, each at a distance from a respective light source such that light rays emerging from the optical elements 250 appear substantially in parallel to each other.

In an embodiment of the invention, ref. FIG. 5, the light receiver 300 comprises a light stop 320 arranged between said image forming optical means 330 and the detector 310, and having an opening to allow passing of light propagating on or close to the optical axis of the image forming optical means.

Figure 3A:
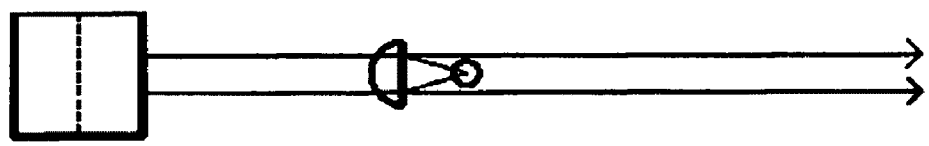
FIG. 3A is a top view drawing of a first variant of the collimated light source of FIG. 2.
Figure 3B:
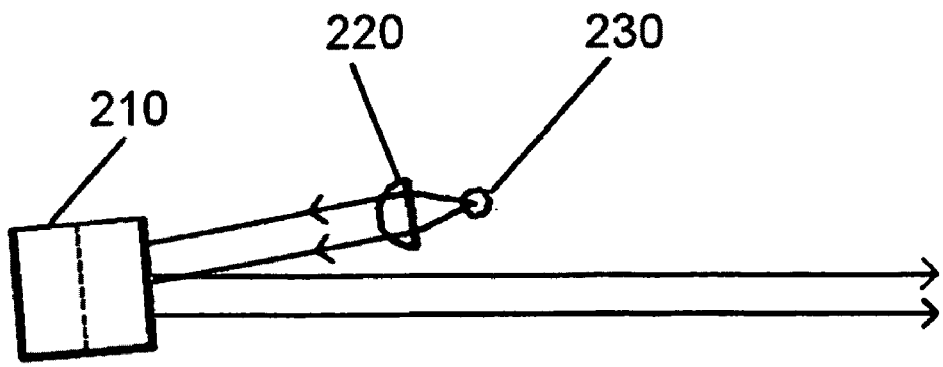
FIG. 3B is a top view drawing of a second variant of the collimated light source of FIG. 2.

According to an aspect of the invention, the detector 310 is an image detector extending along an axis of extension lying in the first plane 500 or a plane obtained by folding said first plane along a folding line, thus appearing "off axis", corresponding to an "off-axis" arrangement being illustrated in FIG. 3B for a collimated light source.

According to a further aspect, the axis of extension of the detector 310 is angled different from a perpendicular to the optical axis, as shown in FIG. 5 by the "tilted" detector 310, such that a proximal part of the first area 400 of the surface being proximal to the light receiver is properly focused at corresponding first one of the image detector and a distal part of the first area 400 of the surface being distal to the light receiver is properly focused at corresponding second end of the image detector.

In an embodiment of the apparatus of the invention, the collimator includes first 220 and second 210 focusing optical elements arranged to focus light in respective, mutually perpendicular planes.

Advantageously, the first focusing optical element 220 may be a cylindrical lens and second focusing optical element 210 is a cylindrical mirror.

Figure 6A:
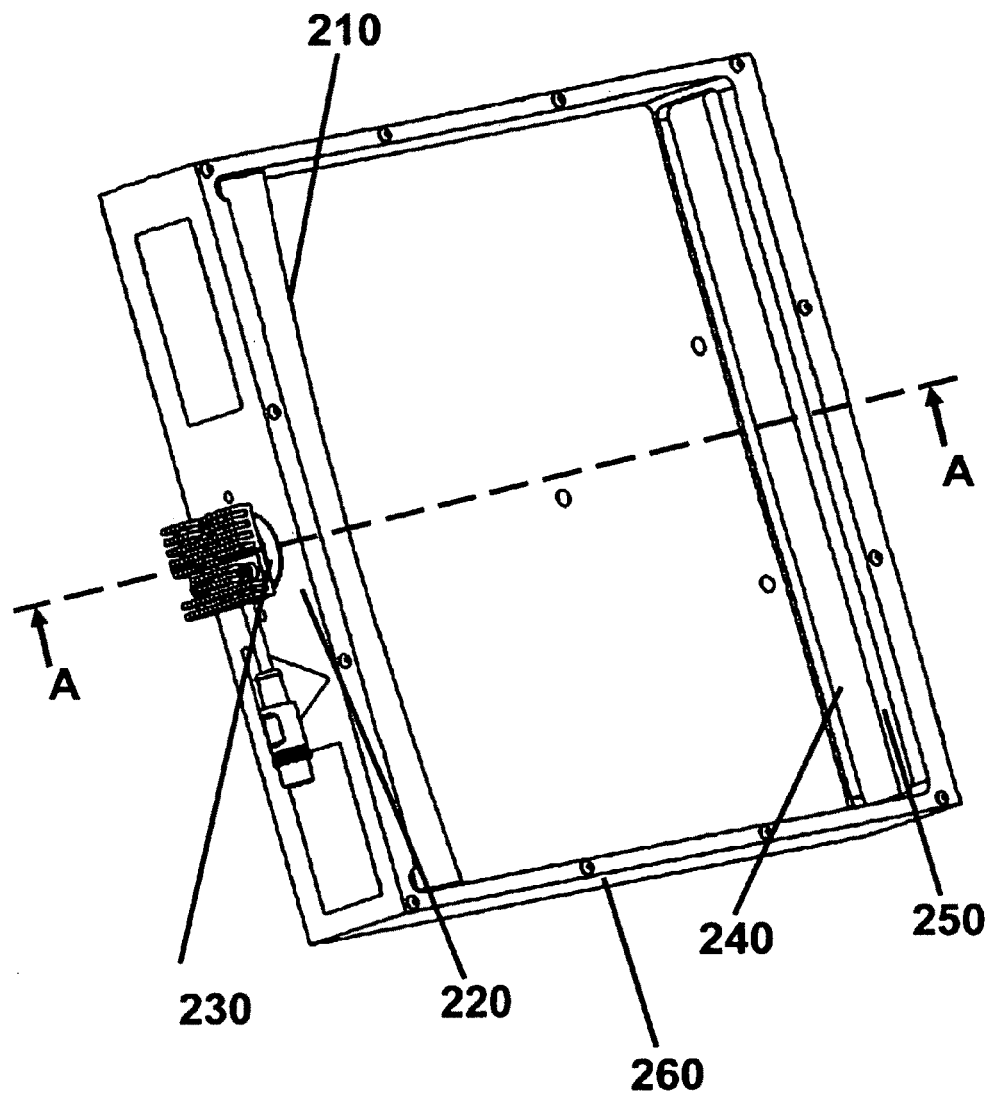
Figure 6B:
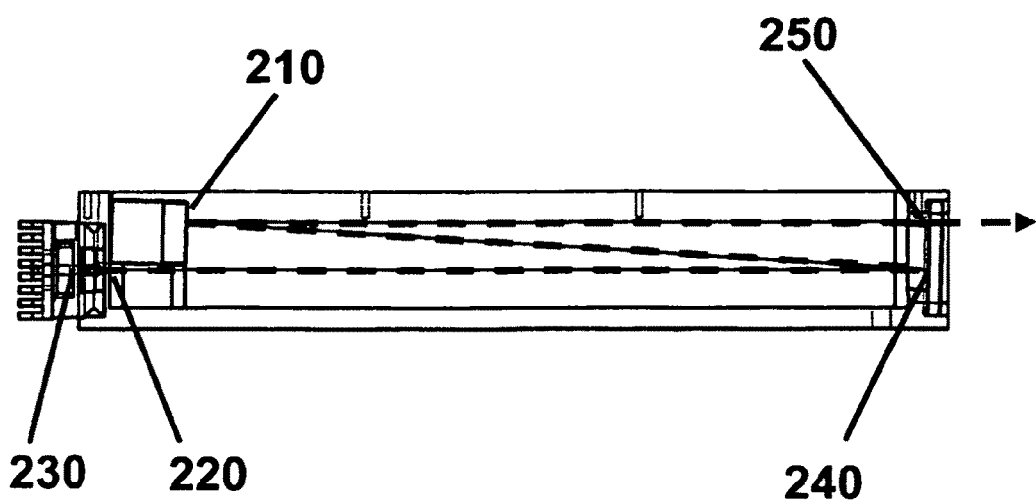

In a compact collimated light source of the invention, an embodiment of which is illustrated in FIGS. 6A and 6B, a folding mirror 240 is included, and arranged in a light path between the first 220 and second 210 focusing, optical elements, all of which are mounted in a housing 260. The light source 230 appears "shifted" with respect to the output from the unit. Some elements indicated by reference signs in FIG. 6A are hidden by the housing 260, but appear in the sectional view of FIG. 6B, the section taken along the line A-A of FIG. 6A.

According to a further aspect of the invention, the folding mirror 240 is a separate element, or may is provided on a surface of first part of an optically transparent element (240, 250), and arranged in respect to the first and second focusing optical elements arranged such that a light beam propagated from the first focusing element 220, and via the folding mirror 240 and then second focusing element 210, to be emitted through a separate exit window 250 or a second, transparent part of the optically transparent element providing the exit window 250.

An apparatus according to the invention should include a conveyor for conveying the board or sheet past the source of collimated light and the detector arrangement, or to convey the source of collimated light and the detector arrangement past the board or sheet, thereby enabling a scanning of the surface of the board or sheet in order to a allow continuous inspection of the entire surface of the board or sheet to be made.

Optionally, the apparatus disclosed above may include a source of collimated light adapted to illuminate simultaneously an upper surface as well as a lower surface of the board or sheet, and, of course, a corresponding detector arrangement adapted to receive simultaneously light reflected off or scattered by the upper surface as well as a lower surface of the board or sheet. Thus, both surfaces of the board or sheet may be inspected at the same time.

The invention claimed is:

1. An apparatus for optically characterizing a surface structure of a board or sheet, the apparatus comprising:
   a light source arranged at a first side of a said board and adapted to illuminate a first area of a surface of said board or sheet by emitting towards said surface a collimated light beam at a first, oblique angle of incidence relative to said surface of said board or sheet,
      wherein the light source comprises an optical collimator adapted to provide said light beam as a broad, collimated light beam having an elongated cross section of a first length, and propagating in a first plane, and the first plane is substantially perpendicular to a plane of said first part of said surface of said board or sheet, and
      wherein the first, oblique angle is such that the first length when projected onto the first surface is substantially equal to or greater than a width of said board or sheet; and
   a light receiver arranged at a second side of a said board or sheet, said second side being substantially opposite to said first side in respect of said board or sheet, said light receiver adapted to receive at least a part of said collimated light beam being reflected off said first area of said surface of said board or sheet, and including a spatial detector adapted to receive by different parts of said detector light of said collimated light beam being reflected off respective, different parts of said first area,
      wherein the detector is an image detector extending along an axis of extension lying in the first plane or a plane obtained by folding said first plane along a folding line, and
      wherein the axis of extension is angled different from a perpendicular to the optical axis, such that a proximal part of the first area of the surface being proximal to the light receiver is properly focused at corresponding first one end of the image detector and a distal part of the first area of the surface being distal to the light receiver is properly focused at corresponding second end of the image detector.

2. The apparatus of claim 1, wherein the light receiver comprises an image forming optical means for imaging onto said detector an image at least a section of said first area, said image forming optical means having an optical axis.

3. The apparatus of claim 2, wherein the image forming optical means comprises a focusing optical element having its optical axis inclined relative to the first area of the surface at an angle that substantially corresponds to an angle at which the collimated light beam is reflected off the first area of the surface by specular reflection.

4. The apparatus of claim 2, wherein the light receiver comprises a light stop arranged between said image forming optical means and the detector, and having an opening to allow passing of light propagating on or close to the optical axis.

5. An apparatus for optically characterizing a surface structure of a board or sheet, the apparatus comprising:
 a light source arranged at a first side of a said board and adapted to illuminate a first area of a surface of said board or sheet by emitting towards said surface a collimated light beam at a first, oblique angle of incidence relative to said surface of said board or sheet,
  wherein the light source comprises an optical collimator adapted to provide said light beam as a broad, collimated light beam having an elongated cross section of a first length, and propagating in a first plane, and the first plane is substantially perpendicular to a plane of said first part of said surface of said board or sheet,
  wherein the first, oblique angle is such that the first length when projected onto the first surface is substantially equal to or greater than a width of said board or sheet,
  wherein the collimator comprises first and second focusing optical elements arranged to focus light in respective, mutually perpendicular planes, and
  wherein the first focusing optical element is a cylindrical lens and the second focusing optical element is a cylindrical mirror; and
 a folding mirror arranged in a light path between the first and second focusing, optical elements,
  wherein the folding mirror is provided on a surface of first part of an optically transparent element, and arranged with the first and second focusing optical elements arranged such that a light beam propagated from the first focusing element and via the folding mirror and the second focusing element is emitted through a second, transparent part of the optically transparent element.

* * * * *